US011972567B2

United States Patent
Lee et al.

(10) Patent No.: US 11,972,567 B2
(45) Date of Patent: Apr. 30, 2024

(54) SYSTEM AND METHOD FOR ANALYZING MEDICAL IMAGES TO DETECT AND CLASSIFY A MEDICAL CONDITION USING MACHINE-LEARNING AND A CASE PERTINENT RADIOLOGY ATLAS

(71) Applicant: The General Hospital Corporation, Boston, MA (US)

(72) Inventors: Hyunkwang Lee, Cambridge, MA (US); Sehyo Yune, Somerville, MA (US); Synho Do, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/055,068

(22) PCT Filed: May 29, 2019

(86) PCT No.: PCT/US2019/034367
§ 371 (c)(1),
(2) Date: Nov. 12, 2020

(87) PCT Pub. No.: WO2019/232027
PCT Pub. Date: Dec. 5, 2019

(65) Prior Publication Data
US 2021/0217167 A1 Jul. 15, 2021

Related U.S. Application Data

(60) Provisional application No. 62/677,216, filed on May 29, 2018.

(51) Int. Cl.
*G06K 9/00* (2022.01)
*G06N 3/045* (2023.01)
(Continued)

(52) U.S. Cl.
CPC ........... *G06T 7/0014* (2013.01); *G06N 3/045* (2023.01); *G16H 30/20* (2018.01); *G16H 50/20* (2018.01);
(Continued)

(58) Field of Classification Search
CPC ......... G06T 7/0014; G06T 2207/10081; G06T 2207/20081; G06T 2207/20084;
(Continued)

(56) References Cited

U.S. PATENT DOCUMENTS 10,475,182 B1 * 11/2019 Chilamkurhy ....... A61B 5/7264
10,892,050 B2 * 1/2021 Zhang ...................... G06N 3/04
(Continued)

FOREIGN PATENT DOCUMENTS

CN 108784655 A * 11/2018 ............... A61B 5/72
WO 2017/106645 A1 6/2017

OTHER PUBLICATIONS

Arbabshirani, M.R., et al., "Advanced machine learning in action: identification of intracranial hemorrhage on computer tomography scans of the head with clinical workflow integration." NPJ Digital Medicine (2018) pp. 1-9.
(Continued)

*Primary Examiner* — Xin Jia
(74) *Attorney, Agent, or Firm* — Quarles & Brady LLP

(57) ABSTRACT

A system for analyzing medical images to detect and classify a medical condition, the system includes an input for receiving a medical image, a convolutional neural network coupled to the input and configured to analyze the medical image to generate a prediction including a probability of the presence of the medical condition in the medical image and an atlas creation module coupled to the convolutional neural network and configured to generate an atlas comprising a set of image features and a set of training images. Each image feature is assigned with at least one training image associated with the medical condition. The system further includes a prediction basis selection module coupled to the convolutional neural network and the atlas and configured to create a prediction basis for the prediction generated by the convolutional neural network.

18 Claims, 10 Drawing Sheets

(51) Int. Cl.
 *G06T 7/00* (2017.01)
 *G16H 30/20* (2018.01)
 *G16H 50/20* (2018.01)

(52) U.S. Cl.
 CPC ............. *G06T 2207/10081* (2013.01); *G06T 2207/20081* (2013.01); *G06T 2207/20084* (2013.01); *G06T 2207/30016* (2013.01)

(58) Field of Classification Search
 CPC ........ G06T 2207/30016; G06T 7/0012; G06N 3/0454; G16H 30/20; G16H 50/20
 See application file for complete search history.

(56) References Cited

U.S. PATENT DOCUMENTS

| | | | |
|---|---|---|---|
| 2017/0200067 A1 | 7/2017 | Zhou et al. | |
| 2019/0122364 A1* | 4/2019 | Zhang | G06K 9/6255 |
| 2019/0251694 A1* | 8/2019 | Han | G06T 7/11 |

OTHER PUBLICATIONS

Chilamkurthy, S. et al., "Deep learning algorithms for detection of critical findings in head CT scans: a retrospective study." Lancet https://doi.org/10.1016/S0140-6736(18)31645-3 (2018).
Clinical and Patient Decision Support Software. Draft Guidance for Industry and Food and Drug Administration Staff (US FDA, 2017).
Desai, V., et al., "Application of deep learning in neuroradiology: automated detection of basal ganglia hemorrhage using 2D-convolutional neural networks." Preprint at https://arxiv.org/abs/1710.03823 (2017).
Grewal, M., et al., "RADNet: Radiologist level accuracy using deep learning for hemorrhage detection in CT scans." 2018 IEEE 15th International Symposium on Biomedical Imaging (ISBI 2018), Washington, DC, USA, 2018, pp. 281-284, doi: 10.1109/ISBI.2018.8363574.
Phong, T.D., et al., "Brain hemorrhage diagnosis by using deep learning." In Proc. 2017 International Conference on Machine Learning and Soft Computing 34-39 (ACM, 2017).
Prevedello, L.M., et al. "Automated critical test Findings identification and online notification system using artificial Intelligence in imaging" Radiology (2017) vol. 285, pp. 923-931.
International Search Report issued for PCT/US2019/034367 dated Aug. 16, 2019.
International Preliminary Report on Patentability issued for PCT/US2019/034367 dated Dec. 1, 2020.

* cited by examiner

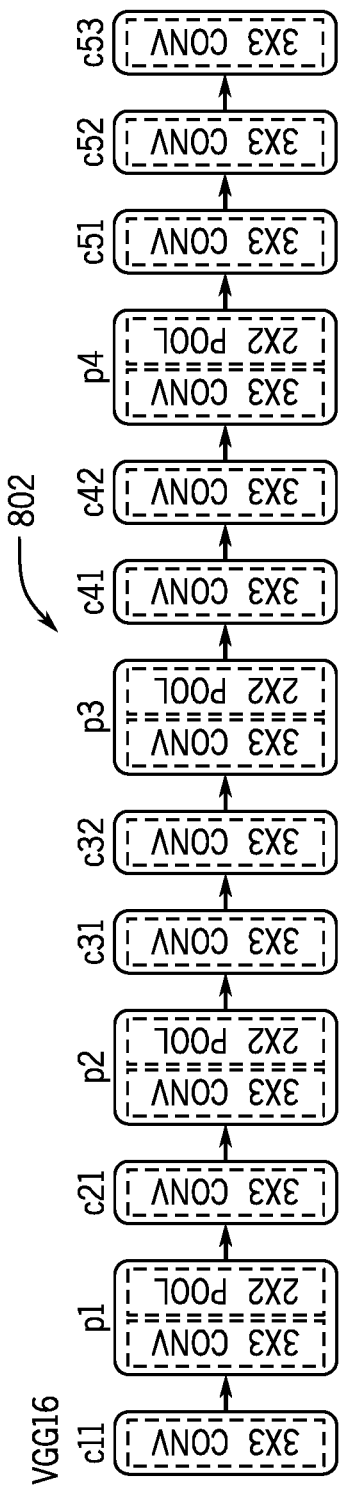
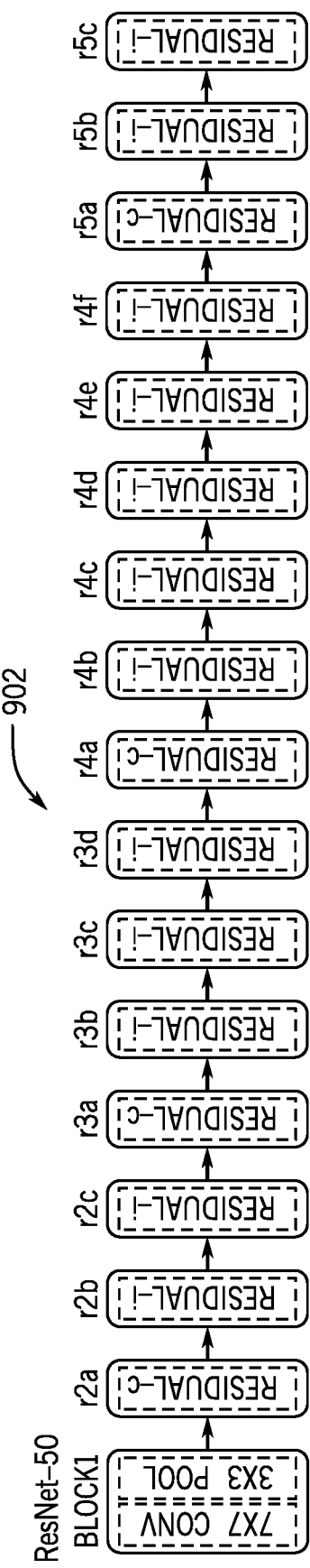
FIG. 8
FIG. 9

SYSTEM AND METHOD FOR ANALYZING MEDICAL IMAGES TO DETECT AND CLASSIFY A MEDICAL CONDITION USING MACHINE-LEARNING AND A CASE PERTINENT RADIOLOGY ATLAS

CROSS-REFERENCE TO RELATED APPLICATIONS

This application is a National Stage of International Application No. PCT/US2019/034367 filed May 29, 2019 which is based on, claims priority to, and incorporates herein by reference in its entirety U.S. Ser. No. 62/677,216 filed May 29, 2018, and entitled "Systems And Methods For A Machine-Learning Based Case-Pertinent Radiology Atlas."

FIELD

The present disclosure relates generally to machine-learning models for analyzing medical images and, in particular, to a system and a method for analyzing medical images using a deep convolutional neural network and a radiology atlas to detect and classify a medical condition.

BACKGROUND

During the past decade, much progress has been made in machine learning as a result of both increased computational power and the accumulation of big data. Advances in image recognition based on deep learning, a subset of machine learning, are changing the landscape of medicine by achieving physician-level performance in various tasks. These breakthroughs can improve diagnostic accuracy, streamline physician workflow, provide expertise to underserved populations and even prompt the discovery of new biological insights. For example, improvements in image recognition via deep learning may allow machine learning algorithms to be applied to automated medical diagnoses that can guide clinical decision-making. However, high-performance deep learning requires large, high-quality training datasets. In addition, these algorithms remain a 'black box' in terms of how they generate the predictions from the input data. The need for big data and the black box problem represent substantial obstacles to the development and translation of medical deep-learning systems into clinical practice.

As mentioned, a first challenge in developing medical imaging deep-learning systems is access to large and well-annotated datasets. Deep learning is unique in its capability of recognizing meaningful patterns from raw data without explicit directions when provided with sufficient examples. To make the most of this capability, previously published medical imaging deep-learning studies that have achieved physician level performance have used over 100,000 images to train the networks. However, collecting and labelling such large datasets is onerous and often infeasible for many researchers. Moreover, institutions are often hesitant to share data with external collaborators because of patient privacy, as well as ethical and legal considerations. Even if a researcher manages to collect such large datasets, labelling and validating big data are expensive and time consuming. A second challenge in developing medical imaging deep-learning systems is that the inner workings and decision-making processes of machine-learning algorithms remain opaque. For machine learning algorithms to be used in clinical practice, it is essential that they can explain the rationale for the recommendations they make. The US Food and Drug Administration requires any clinical decision support software to explain the rationale or support for its decisions to enable the users to independently review the basis of their recommendations. To meet this requirement and gain trust from clinicians, medical deep-learning systems should provide explanations for their outputs. Many existing medical imaging deep learning systems only provide attention maps visualizing important regions for AI prediction without additional explanation. Although attention maps are useful for end users to find the regions of interest identified by the model, they do not fully explain the reasons for the decisions made by the model. Overcoming these two major barriers to training and clinical implementation can facilitate the development and a broader clinician adoption of deep-learning technology into medical practice.

SUMMARY

In accordance with an embodiment, a system for analyzing medical images to detect and classify a medical condition, the system includes an input for receiving a medical image, a convolutional neural network coupled to the input and configured to analyze the medical image to generate a prediction including a probability of the presence of the medical condition in the medical image and an atlas creation module coupled to the convolutional neural network and configured to generate an atlas comprising a set of image features and a set of training images. Each image feature is assigned with at least one training image associated with the medical condition. The system further includes a prediction basis selection module coupled to the convolutional neural network and the atlas and configured to create a prediction basis for the prediction generated by the convolutional neural network by selecting at least one image feature and at least one training image assigned to the selected image feature from the atlas and a display coupled to the convolutional neural network and the prediction basis selection module, the display configured to display at least the prediction and the prediction basis.

In accordance another embodiment, a method for analyzing medical images to detect and classify a medical condition includes receiving a medical image, analyzing the medical image using a convolutional neural network to generate a prediction including a probability of the presence of the medical condition in the medical image and creating a prediction basis for the prediction generated by the convolutional neural network by selecting at least one image feature from an atlas comprising a set of image features and a set of training images. Each image feature is assigned with at least one training image associated with the medical condition. The method further includes displaying at least the prediction and the prediction basis on a display.

BRIEF DESCRIPTION OF THE DRAWINGS

The present disclosure will hereafter be described with reference to the accompanying drawings, wherein like reference numerals denote like elements.

FIG. 8 is a block diagram of a network topology for an example deep convolutional neural network (DCNN) in accordance with an embodiment;

FIG. 9 is a block diagram of a network topology for an example deep convolutional neural network (DCNN) in accordance with an embodiment;

DETAILED DESCRIPTION

Figure 1:
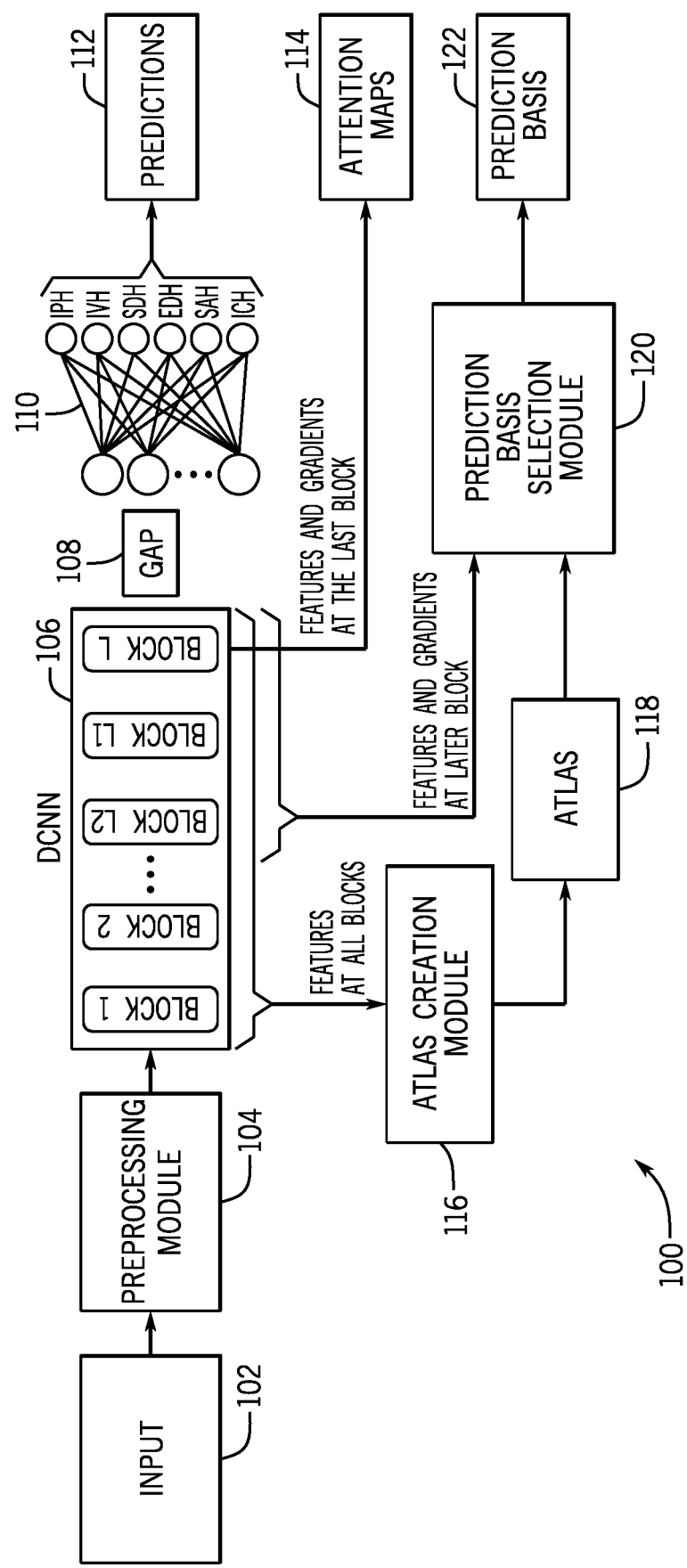
FIG. 1 is a block diagram of a system for detection and classification of a medical condition in accordance with an embodiment.

The present disclosure describes an explainable deep learning system and method for the detection and classification of a medical condition based on analysis of medical images. The system and method utilize a case-pertinent radiology atlas that is used to provide explanation of the output, for example, an explanation of the rationale and support for a predicted diagnosis of a medical condition. The system and method utilize a deep learning system that analyzes medical images and predicts outcome diagnosis. In addition, the system and method generate a radiology atlas that contains representative visual depictions (e.g., training images from a dataset used to train the deep learning system) of significant features for the medical condition during training. During analysis of a given input image, the system extracts training images from the radiology atlas that contain the features that were considered with high importance when making a prediction for a given input image. In an embodiment, the deep learning system is trained using a small and imbalanced training dataset (e.g., fewer than 1000 cases).

The machine-learning based case-pertinent radiology atlas allows the deep learning system to detect and classify a medical condition from medical images accurately and efficiently and to provide training images pertinent to a given input image as the basis of its prediction. In an embodiment, in addition to attention maps the system and method for analyzing medical images provides a prediction basis as an output consisting of representative training images that contain similar significant features as an additional explanation to allow end users (e.g., a radiologist) to come to their informed clinical decisions. An explainable system may facilitate and accelerate the adoption of deep-learning systems into clinical practice. While the following description of FIGS. 1-12 is discussed in terms of the analysis of computed tomography (CT) images to detect and classify intracranial hemorrhage (ICH), it should be understood that the system and method described herein, including the radiology atlas, may be used for analyzing any type of medical image (e.g. CT, magnetic resonance (MR), X-ray, etc.) and to detect and classify (e.g., predict a diagnosis) various types of medical conditions.

In an embodiment, an understandable (or explainable) deep-learning system is used to detect acute intracranial hemorrhage (ICH) (the medical condition type) and classify five ICH subtypes from unenhanced head computed-tomography (CT) scans. The five ICH subtypes are intraparenchymal hemorrhage (IPH), intraventricular hemorrhage (IVH), subdural hemorrhage (SDH), epidural hemorrhage (EDH) and subarachnoid hemorrhage (SAH). Acute ICH is a potentially life-threatening condition that requires fast detection, and it must be rapidly distinguished from ischemic stroke to prompt appropriate treatment and mitigate neurological deficit and mortality. As many facilities do not have sub-specialty-trained neuroradiologists, especially at night and on weekends, non-expert healthcare providers are often required to make a decision to diagnose or exclude acute hemorrhage. A reliable second opinion that is trained by neuroradiologists can help make healthcare providers more efficient and confident to enhance patient care, empower patients and cut costs.

FIG. 1 is a block diagram of a system for detection and classification of a medical condition in accordance with an embodiment. The system 100 includes an input 102, a preprocessing module 104, a deep convolutional neural network (DCNN) 108, an atlas creation module 116 and a prediction basis selection module 120. Input 102 is configured to receive an input image, for example, the input image(s) may be training images for training of the system 100 or an image to be analyzed by the trained system 100. In an embodiment where the system is used to detect and classify ICH, the input images (for training and for analysis) are unenhanced CT images. As discussed further below, in an embodiment the training image dataset used to train the system 100 is a small and imbalanced dataset (e.g., fewer than 1000 cases). The image received at input 102 may include a plurality of slices, for example, 2D axial slices from a head CT scan. An image received at input 102 (or a slice of the 3D scan received at input 102) is provided to the preprocessing module 106. As discussed further below, the preprocessing module 104 is configured to perform various pre-processing techniques to improve performance of the system 100. In addition, various optimization techniques (discussed further below) may be utilized to improve performance of the system 100. In an embodiment, the pre-processing techniques performed by the preprocessing module 104 and the optimization techniques are performed iteratively. Greater performance gains may be achieved by iteratively adding pre-processing and network optimization techniques.

The preprocessed image (or slice) is analyzed by the DCNN 106, including a global average pooling layer 108, a fully connected layer 110 and an element-wise sigmoid layer (not shown). In an embodiment, the DCNN includes a plurality of DCNNs. In one example, DCNN 106 consists of a VGG16, a ResNet-50, an Inception-v3, and an Inception-ResNet-v2. In an embodiment, each DCNN used may be pre-trained using the ImageNet image database, for example, a subset of the ImageNet used for the classification task in the ImageNet Large Scale Visual Recognition Challenge (ILSVRC) 2012. The pre-trained DCNN models are then fine-tuned with a training dataset specific to the medical condition, e.g., ICH. As mentioned above, in an embodiment the medical condition specific training dataset may be a small and imbalanced training dataset (e.g., fewer than 1000 cases). The images in the training dataset may be received from, for example, a picture archiving and communications system and may be, for example, DICOM (digital imaging and communications in medicine) images. In an embodiment, the images in a training dataset may be labeled by one or more radiologists, including subspecialty radiologists. For the example ICH detection and classification system, each slice in the training dataset may be labeled as one or more of the following: no hemorrhage, IPH, IVH, SDH, EDH or SAH. The training dataset may be imbalanced because of low incidences of certain ICH subtypes in the patient population of the images in the training dataset. The ICH training dataset may include both standard and denoised CT images.

The DCNN 106 is configured to generate a prediction 112 that indicates if a medical condition (e.g., a ICH) has been detected (e.g., the probability of the condition) and a classification of a detected condition (e.g., one of the five ICH subtypes IPH, IVH, SDH, EDH, SAH). For example, the prediction 112 may indicate the probability of the presence of each subtype of ICH on all slices in the input scan as well as a final prediction for each slice. In an embodiment, the DCNN 106 generates an output based on an ensemble model that combines the probabilities from the plurality of DCNNs. For example, the ensemble model may be defined as the unweighted average of the probabilities of the presence of ICH predicted by each of the DCNNs. In an embodiment, ICH classification is a multi-label classification problem with five binary outputs predicting the presence of each ICH subtype. Each input image may be labelled as one or more ICH subtype. The input is, for example, a 2D axial slice from a head CT scan x and the output is y={$y_1$, $y_2$, $y_3$, $y_4$, $y_5$} that includes the probability of the presence of IPH, IVH, SDH, EDH and SAH, respectively. The sum of the binary cross entropy (BCE) losses of the five outputs for a single instance is given by equation (1):

$$L_{BCE}(x, y) = -\sum_{c=1}^{5} y^c \ln \hat{y}^c + (1 - y^c)\ln(1 - \hat{y}^c) \quad (1)$$

where $y^c$ indicates the probability of the presence of a class label c that an algorithm predicts given an input image x. To counteract the skewed distribution of the training data, an output may be added that predicts the probability of any type of ICH, in addition to the five binary outputs to predict each type of hemorrhage: IPH, IVH, SDH, EDH and SAH. Accordingly, slice level outputs were aggregated to a case level output by defining the presence of a positive ICH subtype on any slice. This allows the DCNN 106 to learn the general representations of ICH, enhancing the overall sensitivity. In an embodiment, the ICH binary value was introduced to update the output of the network to y={$y_1$, $y_2$, $y_3$, $y_4$, $y_5$, $y_6$}, giving the probabilities of IPH, IVH, SDH, EDH, SAH and ICH, respectively. The multi-label classification task was then reformulated into a binary classification, with ICH as positive if one or more of the subtype outputs were positive and negative if not. In addition, additional costs may be imposed on the DCNN 106 model for misclassifying positive instances by weighting the BCE loss function by the ratios of positive and negative examples in each of the binary outputs. The modified BCE loss function is given by equations (2) and (3):

$$L_{W-BCE}(x, y) = -\sum_{c=1}^{6} \alpha_p^c y^c \ln \hat{y}^c + \alpha_N^c (1 - y^c)\ln(1 - \hat{y}^c) \quad (2)$$

$$\alpha_p^c = \frac{|P^c| + |N^c|}{2|P^c|}, \alpha_N^c = \frac{|P^c| + |N^c|}{2|N^c|} \quad (3)$$

where $|P^c|$, $|N^c|$ are the total numbers of positive and negative instances of a class label c, and $\alpha_p^c$, $\alpha_N^c$ are the corresponding loss weights. The balancing factors were calculated on the basis of heuristics.

The system 100 generates an attention (or activation) map 114 for each ICH positive result based on the features and gradients at the last block in the DCNN 106. The atlas creation module 116 and the prediction basis selection module 120 form a visualization tool that may be used to generate an atlas (or radiology atlas) 118 and display a prediction basis 122. As discussed further below, the atlas 118 is created using a training dataset specific to the medical condition, e.g., ICH. The atlas creation module 116 receives features from all of the blocks (or layers) of the DCNN 106. The atlas 118 includes a set of training images (or training image patches) and attention maps that correspond to significant features of each of the five ICH subtypes. The prediction basis selection module 120 receives features from the later blocks (or layers) of the DCNN 106 and retrieves training images from the atlas 118 that contain significant features relevant to the analyzed input image to provide a prediction basis 122. The training images retrieved from the atlas 118 as a prediction basis provide an explanation for the predictions 112 made by the system 100 based on the analysis of the input image. Showing morphologically similar, prelabeled cases of specific hemorrhage subtypes compared to the input image being analyzed can be especially helpful for user with insufficient experience with ICH. By looking at the attention map 114 and the prediction basis 122, a user can understand the prediction 112 of the system 100. This may increase confidence levels of clinicians for making or excluding a diagnosis and may also provide educational feedback at the point-of-care that will benefit non-experts such as residents, general radiologists, and other non-radiologist clinicians.

Figure 2:
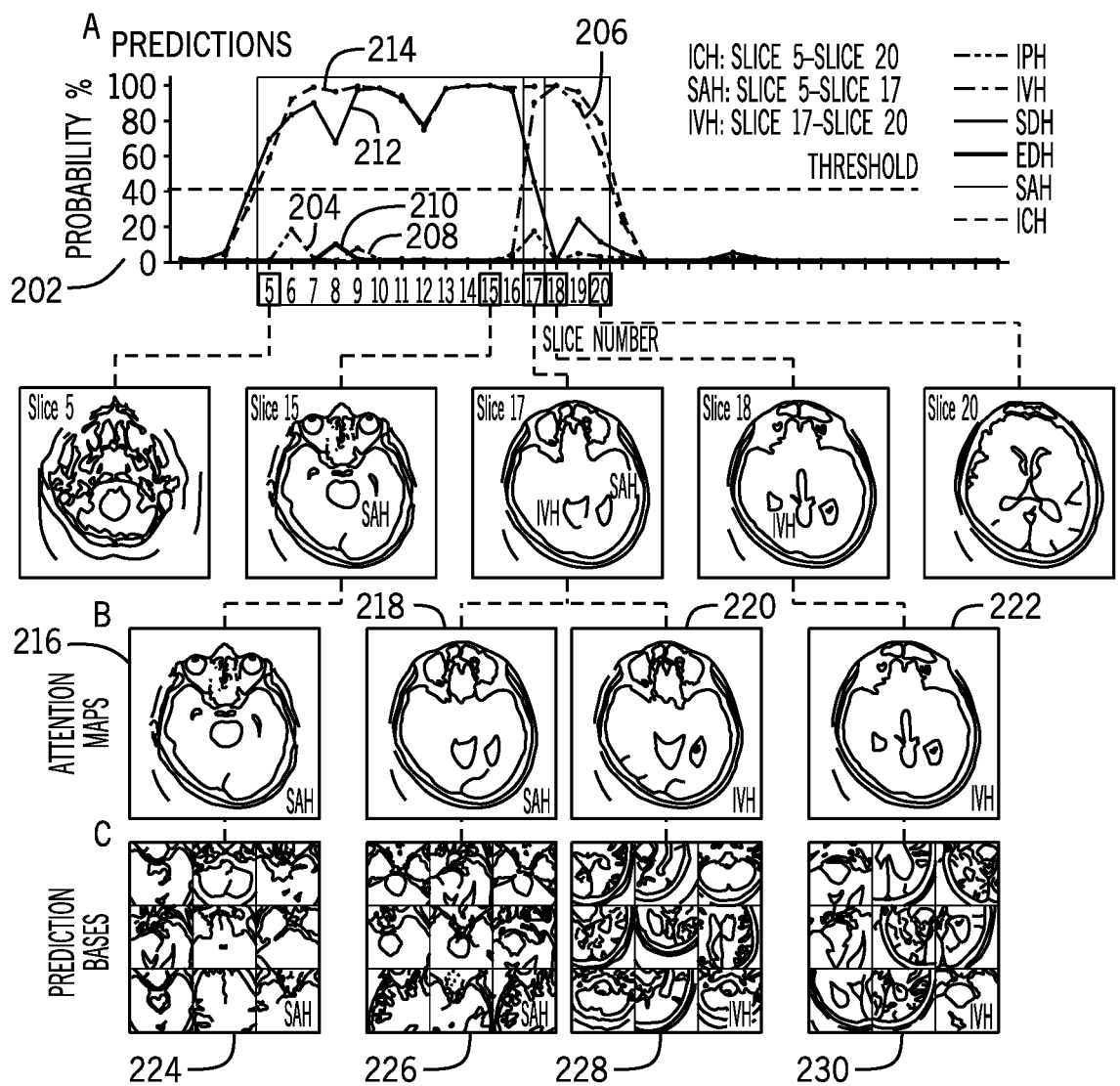
FIG. 2 illustrates example outputs for a deep learning system for detecting and classifying intracranial hemorrhage (ICH) in accordance with an embodiment.

As mentioned, the system 100 analyzes an image and generates a prediction 112, an attention map 114 and a prediction basis 122. FIG. 2 illustrates example outputs for a deep learning system for detecting and classifying intracranial hemorrhage (ICH) in accordance with an embodiment. In FIG. 2, a graph 202 shows probabilities of the presence of each type of ICH generated by the system 100 (shown in FIG. 1) for analysis of an example CT scan. FIG. 2 shows the probabilities for the presence of IPH 204, IVH 206, SDH, 208, EDH 210, SAH 212 and ICH 214. A graph such as graph 202 may be displayed to provide the prediction 112 (shown in FIG. 1) output. For each ICH positive case, an attention map 216, 218, 220, 222 may be generated that indicates significant pixels in the analyzed image for the prediction by the system to the target label and may be displayed to a user. In one embodiment, the attention maps 216, 218, 220, 222 may be color-coded to indicate the significant pixels in the analyzed image. Another output of the system 100 (shown in FIG. 1) is a prediction basis 224, 226, 228, 230. Each prediction basis 224, 226, 228, 230 includes training images retrieved from the atlas 118 (shown in FIG. 1) that are associated with or assigned to the features that are most relevant to the analyzed image to explain the prediction of a particular ICH subtype.

Figure 3:
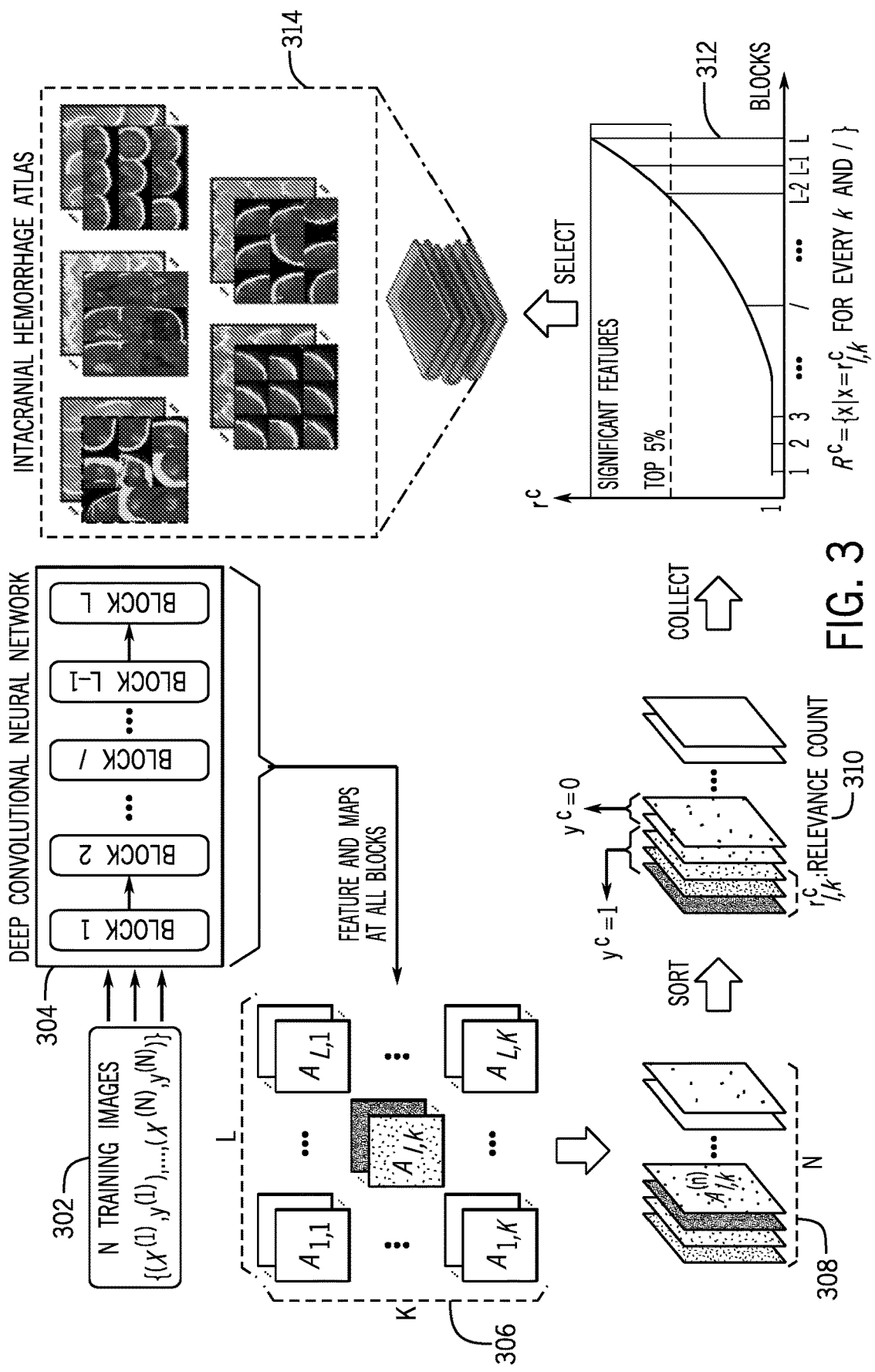
FIG. 3 is a diagram of a process for generating an atlas for use in providing a prediction basis in accordance with an embodiment.
Figure 4:
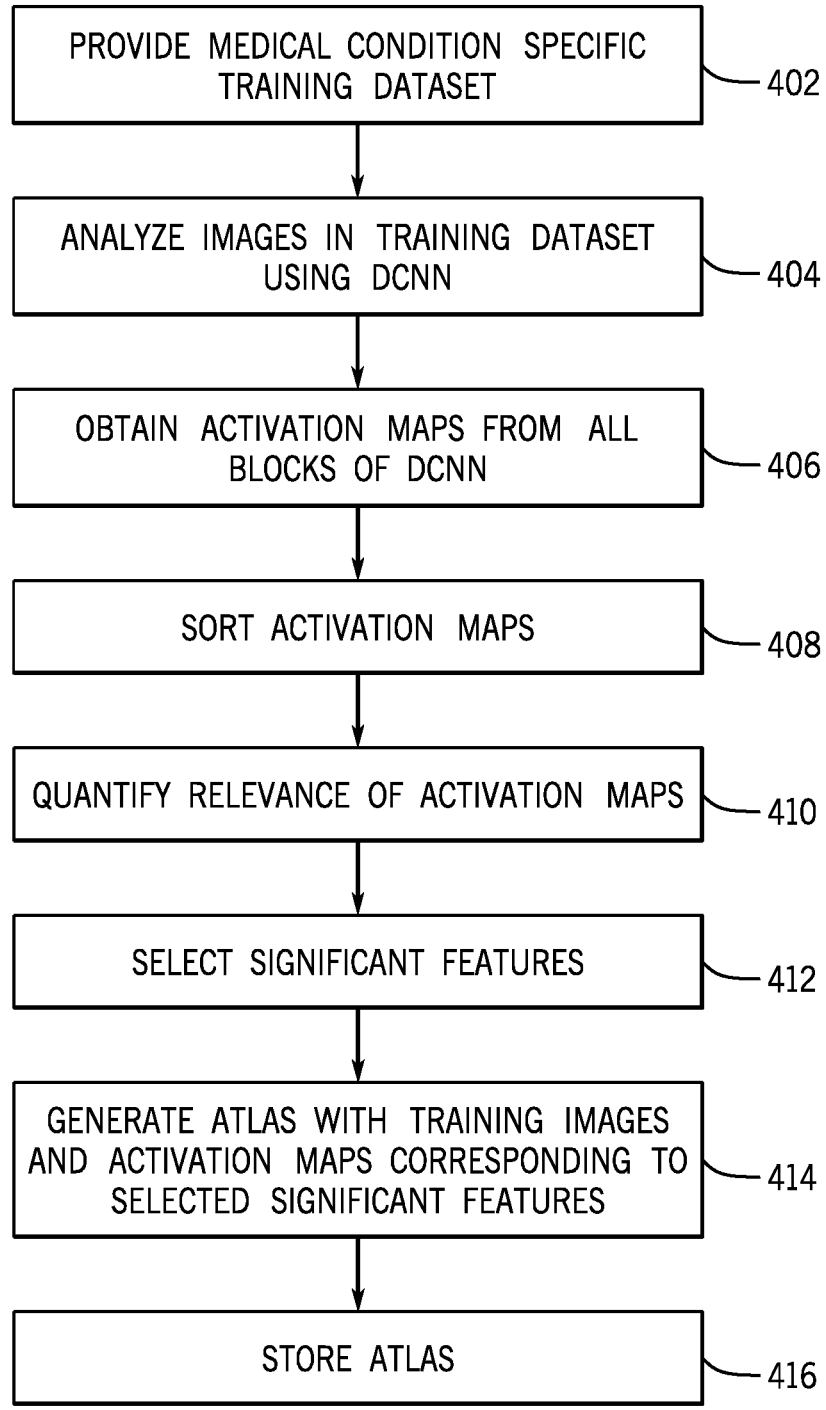
FIG. 4 illustrates a method for generating an atlas for use in providing a prediction basis in accordance with an embodiment.

As mentioned above, atlas creation module 116 (shown in FIG. 1) is used to create an atlas 118 (shown in FIG. 1). FIG. 3 is a diagram illustrating a process for generating an atlas in accordance with an embodiment and FIG. 4 illustrates a method for generating an atlas in accordance with an embodiment. Referring to FIGS. 3 and 4, the medical condition (e.g., ICH) specific training dataset (including training images) used to train the DCNN 106 (shown in FIG. 1), is provided again to the fully trained DCNN at blocks 302 and 402. As discussed above, the training dataset contains various representations of each ICH subtype. All training images are fed through the trained network at blocks 304 and 404 to obtain the corresponding filter responses at each block (or layer) of the DCNN. At block 306 and 406, N activation maps were generated for each filter from each block. At block 308 and 408, the activation maps are sorted by their maximum activation values from highest to lowest. The relevance of each activation map to a particular label is quantified at blocks 310 and 410. In an embodiment, the relevance of each activation map to a particular label is quantified by counting the number of activation maps assigned to the label consecutively from the top. For example, if the activation map with the highest maximum value is labelled as SAH and IPH, the second highest is labelled as SAH and the third is labelled as SDH, the relevance count is 2 for SAH, 1 for IPH and 0 for all other labels. At blocks 312 and 412, the most relevant or significant features for each subtype are selected. In one embodiment, all activation maps at all blocks for each label may be sorted from the highest to the lowest relevance count and a certain percentage of them, for example, the top 5% may be selected as having salient features to best represent the image assigned with the label. as components of the atlas. At blocks 314 and 414, an atlas is generated using the activation maps and corresponding image patches (e.g., the training images) for the selected features. In an embodiment, each selected feature that is associated with the medical condition is assigned or associated with at least one training image. At block 416 of FIG. 4, the atlas may be stored, for example, in a computer memory.

Figure 5:
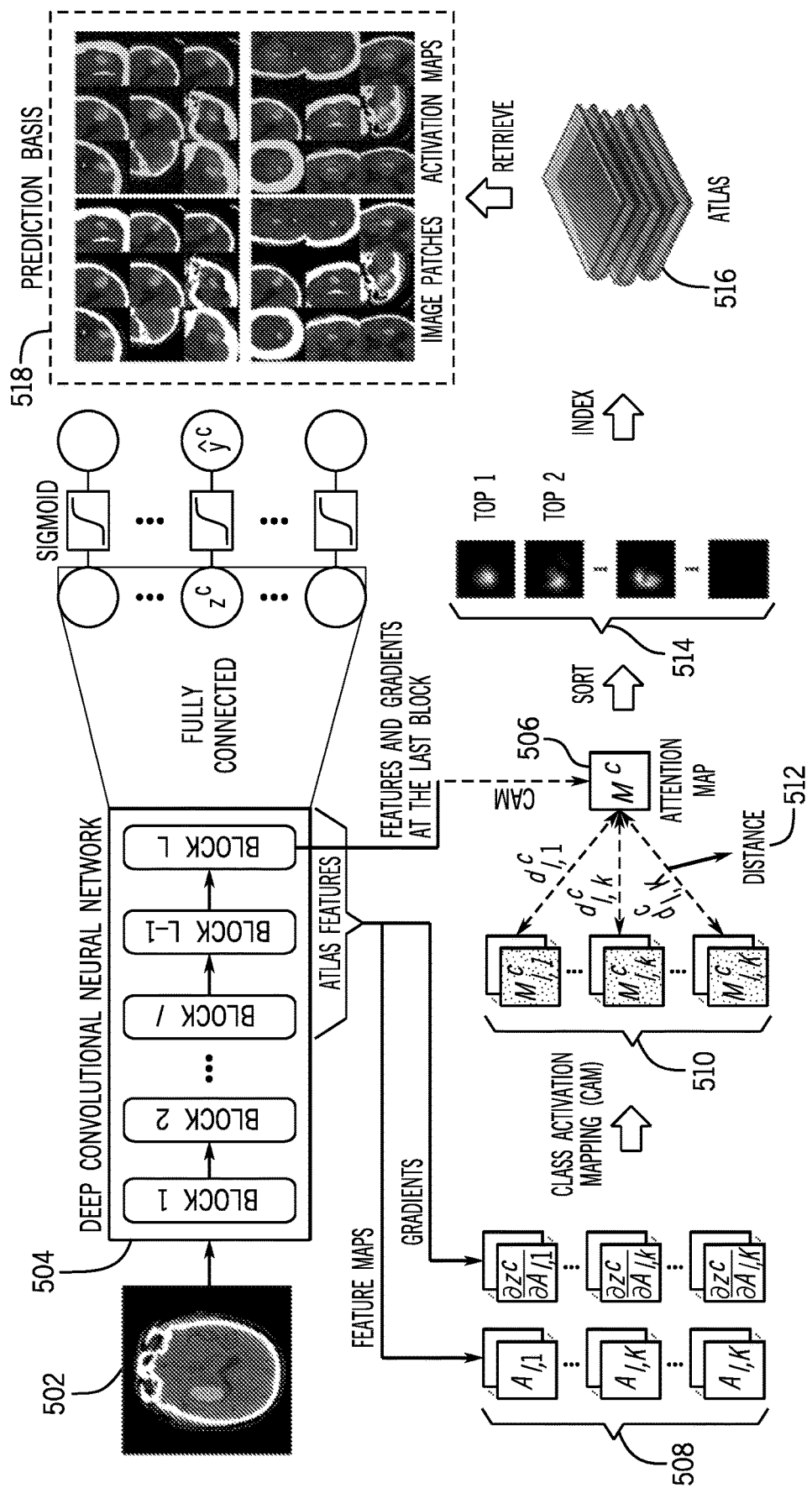
FIG. 5 is a diagram of a process for providing a prediction basis for a predicted diagnosis in accordance with an embodiment.
Figure 6:
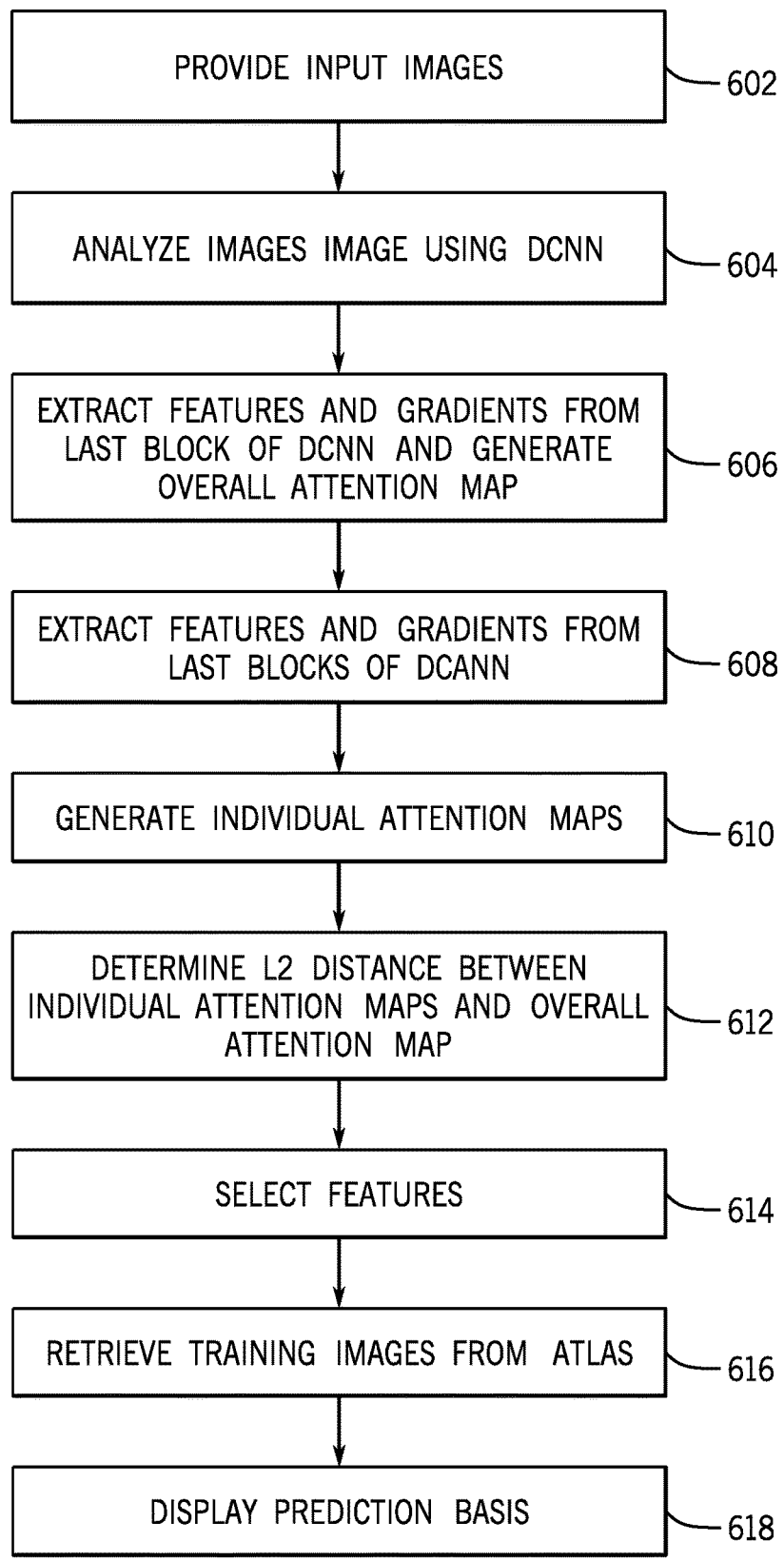
FIG. 6 illustrates a method for providing a prediction bases for a predicted diagnosis in accordance with an embodiment.

As discussed above, the atlas may be used to generate a prediction basis. FIG. 5 is a diagram illustrating a process for determining a prediction basis in accordance with an embodiment and FIG. 6 illustrates a method for determining a prediction basis in accordance with an embodiment. Referring to FIGS. 5 and 6, at blocks 502 and 602, an image is provided to an input (e.g., input 102 shown in FIG. 1) of a DCNN 504. The image is analyzed by the DCNN at blocks 504 and 604. At blocks 506 and 606, features and corresponding gradients from the final block (or convolutional layer) of the DCNN are extracted and used to generate an attention map that highlights the important regions relevant to the predictions of the model. In an embodiment, a class activation mapping (CAM) technique may be applied to generate the attention map. The CAM technique generates attention maps highlighting the important regions in a test image for the model prediction to a target label. The mapping equation is given by equation (4):

$$M^c = ReLU\left(\sum_k A_{L,k} \cdot \frac{1}{S_L} \sum_i \sum_j \frac{\partial z^c}{\partial A_{L,k}}\right) \quad (4)$$

where $z^c$ is a class score (logit) before being fed through the sigmoid function, $S_L$ is the size of each feature map from the last block L, and ReLU corresponds to a rectified linear unit nonlinear function. $M^c$ is the attention map generated using CAM with all feature maps $A_L$ from the last block L. At blocks 508 and 608, features maps and the corresponding gradients are extracted from the later blocks of the DCNN 504. At blocks 510 and 610, individual attention maps may be generated using the CAM technique. CAM can be utilized to generate individual attention maps $M_{L,k}^c$ for the features using the equation (5):

$$M_{L,k}^c = ReLU\left(A_{L,k} \cdot \frac{1}{S_L} \sum_i \sum_j \frac{\partial z^c}{\partial A_{L,k}}\right) \quad (5)$$

where $S_L$ is the size of each feature map from the block L. At blocks 512 and 612, L2 distances between each of the individual attention maps and the overall one are calculated. In an embodiment, the individual attention maps $M_{L,k}^c$ and the overall one $M^c$ are L2-normalized and the L2 distances between them are then computes using the equation (6):

$$d_{L,k}^c = \left\| \frac{M_{L,k}^c}{\|M_{L,k}^c\|_2} - \frac{M^c}{\|M^c\|_2} \right\| \quad (6)$$

At blocks 514 and 614, the features (and attention maps) are sorted by distance from lowest to highest and a set of the features that are significant (e.g., the attention maps with the lowest L2 distance) for the result (or prediction) by the system are selected. For example, the top five features which are significant for the result (or prediction) by the system may be selected. At blocks 516 and 616, the selected features (or attention maps) are used as an index to retrieve representative training images from the atlas with similar significant features to provide a prediction basis of the prediction of the system for the analyzed image. The prediction basis (i.e., the training images retrieved from the atlas) may be displayed to the user at blocks 518 and 618.

As mentioned above, a preprocessing module 104 (shown in FIG. 1) may be configured to perform various preprocessing techniques to improve performance of the system 100 (shown in FIG. 1). In an embodiment, the preprocessing module may perform real-time data augmentation by applying geometric transformation and a nonlinear denoising filtering step to improve the generalizability of the model to different rotations, scales, translations and noise. In addition, the preprocessing module may perform multi-window conversion and slice interpolation. These techniques may be used to address the relatively small size of the training dataset and are based on the workflow of radiologists. High performance may be achieved from a relatively small-sized training dataset by mimicking the workflow of radiologists.

Figure 7:
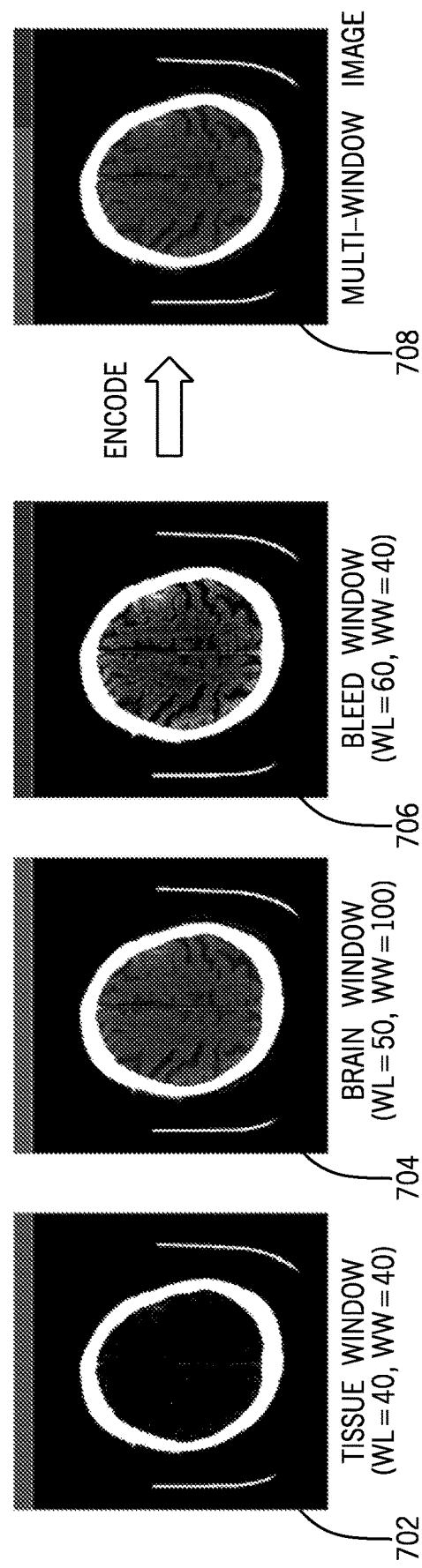
FIG. 7 shows an example multi-window conversion in accordance with an embodiment.

Medical images can range from 12-bits to 16-bits with corresponding greyscale resolutions of 4,096 to 65,536 shades of grey per pixel. This level of data is beyond the limits of human vision, and most medical displays support only 8-bit resolution. For these reasons, CT images presented on digital displays are viewed applying predefined window levels and widths. Different window settings can increase the conspicuity of certain pathologies. During clinical interpretation, radiologists adjust the window width (WW) and window-level (WL) display settings to increase the conspicuity of subtle, potentially significant abnormalities (for example, 'hemorrhage-specific' WL display settings, with greyscale values preset to the typical CT density range of ICH). To mimic this approach, a multi-window conversion technique may be utilized by generating three 8-bit greyscale images with different WL settings and encoding them into a multi-window image in RGB (red, green and blue) with the following: tissue window (WL=40, WW=40) for the red channel; brain window (WL=50, WW=100) for the green channel; and blood window (WL=60, WW=40) for the blue channel. FIG. 7 shows an example multi-window conversion in accordance with an embodiment. FIG. 7 shown a tissue window 703, a brain window 704, a blood window 706 and a multi-window image 708. Encoding the input image into a multichannel composite with standard and customized WL settings allows the system to consider multiple versions of the input image. This improves performance, especially for detecting subtle lesions. In an embodiment, simulating standard radiologist practices to set a narrow WW greyscale display to detect subtle hemorrhage also improves led to a higher performance than using full range 12-bit images. This multi-window conversion is not specific to intracranial pathology and can be optimized for other clinical applications.

The pre-processing module 104 (shown in FIG. 1) may also be configured to perform slice interpolation. Slice interpolation may be used to mimic how radiologists integrate information from all adjacent images of a contiguous three-dimensional (3D) volume concurrently, rather than examine each single axial 2D slice in isolation. Interpolated images from adjacent slices were provided to the system with a modified loss function during training to imitate the 3D integration of image interpolation by radiologists. This technique may be used to reduce the false positive interpretation by the system of partial volume effects and intracranial calcifications. The slice interpolation technique allows the system to take into account neighboring slices and reduce false positive rates. During training, input image x, and label y, are fed through the DCNN 106 (shown in FIG. 1) together with interpolated data with adjacent slices to optimize the modified BCE loss function. The equations to compute interpolated images and labels are given by equation (7):

$$x_{S,S-1}=\beta x_S+(1-\beta)x_{S-1}, y_{S,S-1}=\beta y_S+(1-\beta)y_{S-1}$$

$$x_{S,S+1}=\beta x_S+(1-\beta)x_{S+1}, y_{S,S+1}=\beta y_S+(1-\beta)y_{S+1} \quad (7)$$

where $(x_S, y_S)$ correspond to the image and the label of the sth slice, $(x_{S,S-1}, y_{S,S-1})$ and $(x_{S,S+1}, y_{S,S+1})$ are images and labels of interpolated data from one slice lower (s−1th) and upper (S+1th), respectively. In an embodiment, the interpolation ratio β may be randomly selected from the range of 0.5<β<1.0 on every training batch. If an input image is the first or the last slice of the 3D scan, two interpolated slices may be created from the existing neighbor using two different interpolation rations $\beta_1$ and $\beta_2$. After training, varying degrees of interpolation may be utilized for classification, for example 3, 5, 7 and 9. An interpolation degree n indicates the number of images to be used for predicting a single image. For degree 3, one original image and two interpolated images are generated. For degree 5, one original image and four interpolated images are created. For degree 7, one original image and six interpolated images are generated. For degree 9, one original image and eight interpolated images are created. The final prediction of the target slice may be constructed by taking a linear combination of multiple probabilities from the generated images with the corresponding interpolation ratios. In an embodiment, the best interpolation degree was selected for each of the DCNN models used in DCNN 106 (shown in FIG. 1) based on the performance of the model using a validation dataset.

Figure 10:
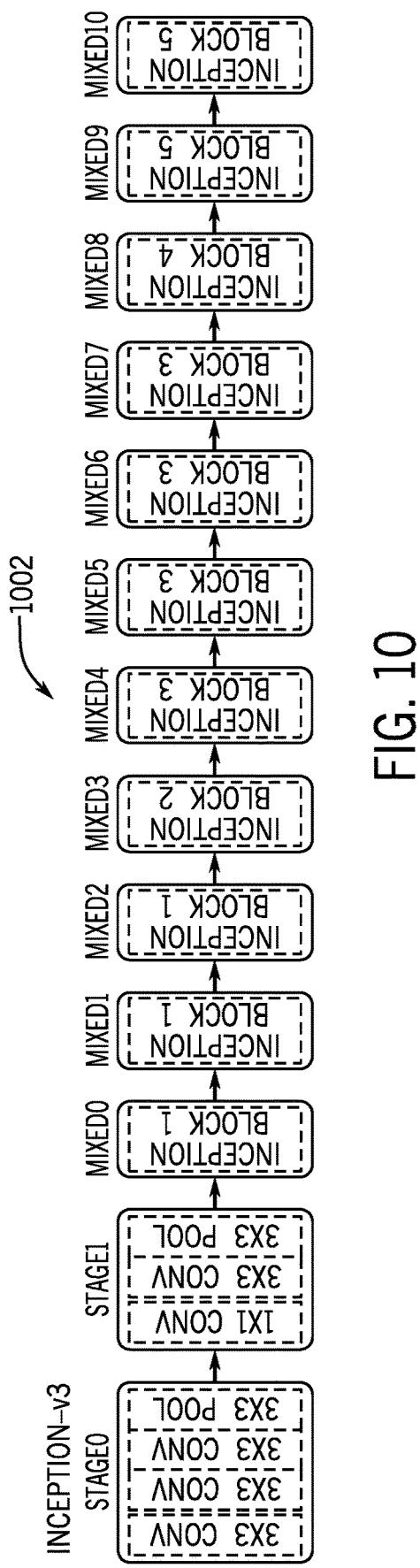
FIG. 10 is a block diagram of a network topology for an example deep convolutional neural network (DCNN) in accordance with an embodiment.
Figure 11:
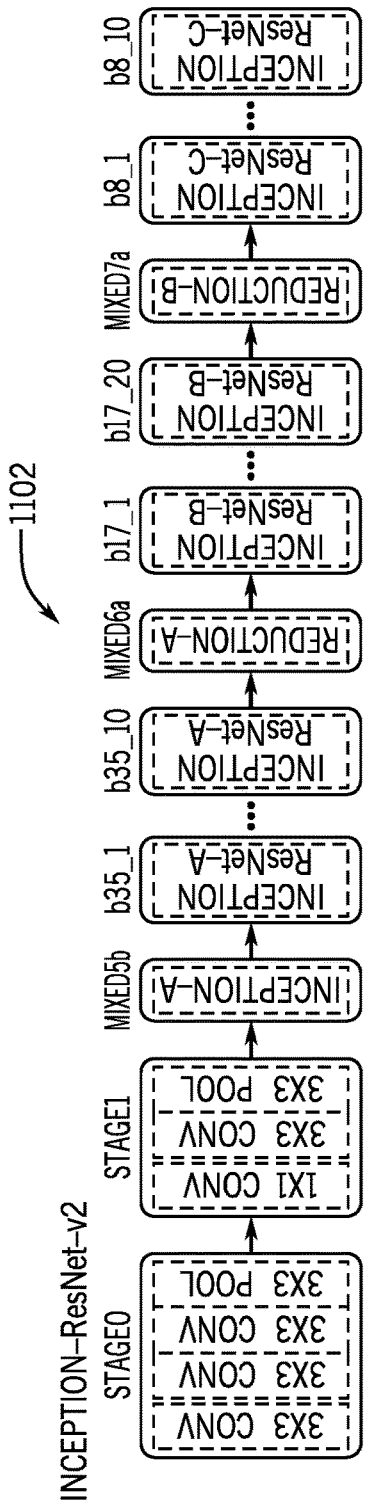
FIG. 11 is a block diagram of a network topology for an example deep convolutional neural network (DCNN) in accordance with an embodiment and FIG. 12 is a block diagram of an example computer system in accordance with an embodiment.

As mentioned above, the DCNN 106 may include a plurality of DCNNs in an embodiment. FIGS. 8-11 show the network topologies of four example DCNN models that may be used in various embodiments. In each of FIGS. 8-11, the network topologies are shown before the last fully-connected layer. FIG. 8 is a block diagram of a network topology for a VGG16 network 802. VGG16 is composed of a sequence of convolutional and pooling layers with a kernel size of 3×3 and 2×2, respectively. FIG. 9 is a block diagram of a network topology for a ResNet-50 network 902. ResNet-50 consists of a convolutional and a pooling layer in the earlier parts of the network, and sequential residual building blocks in the later parts. FIG. 10 is a block diagram of a network topology for an Incenption-v3 network 1002. Inception-v3 is comprised of a sequence of convolutional, pooling layers, and inception modules. FIG. 11 is a block diagram of a network topology for an Inception-ResNet-v2 network 1102. Inception-ResNet-v2 is comprised of inception modules with residual connections.

Figure 12:
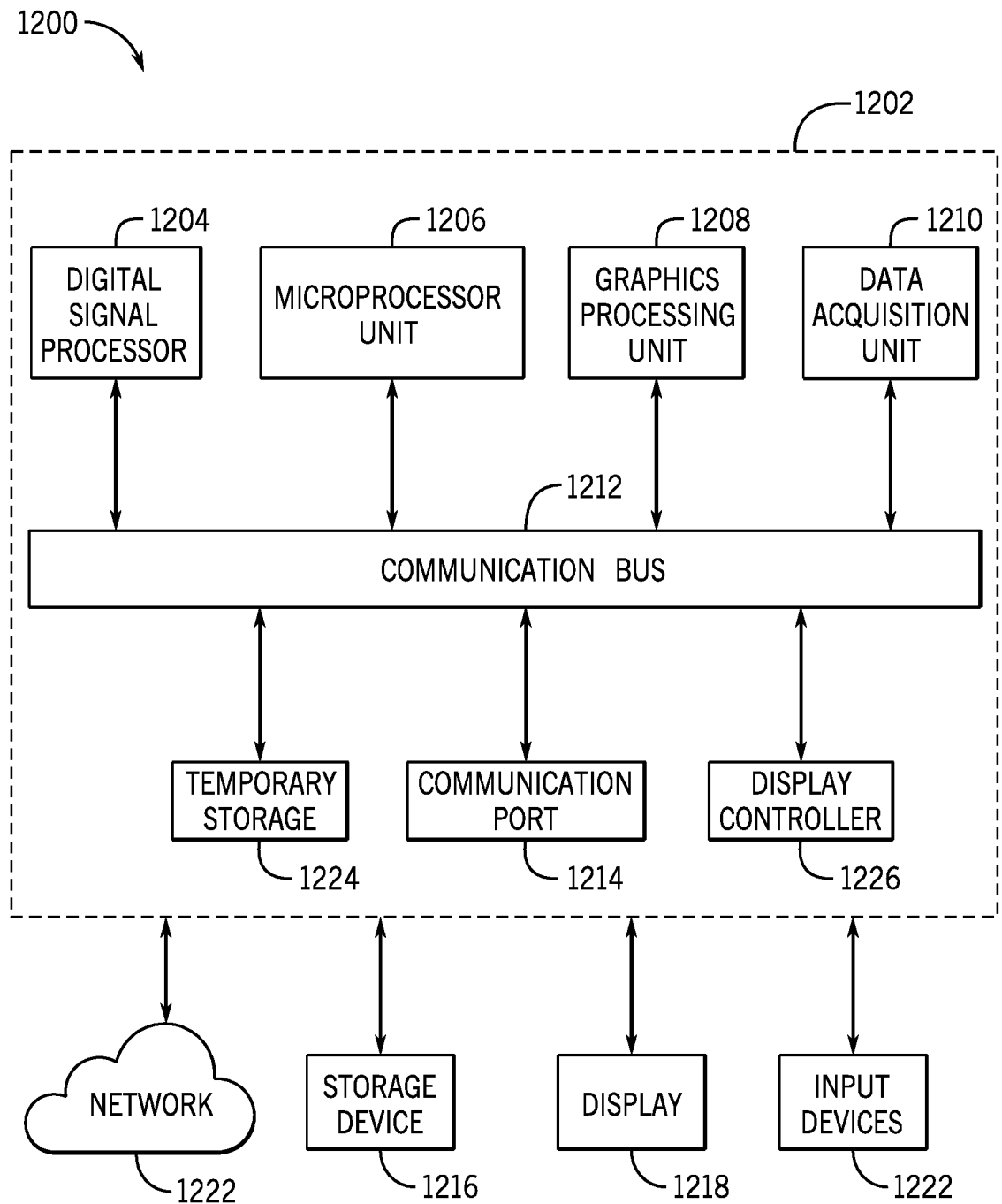

FIG. 12 is a block diagram of an example computer system in accordance with an embodiment. Computer system 1200 may be used to implement the methods described herein. In some embodiments, the computer system 1200 may be a workstation, a notebook computer, a tablet device, a mobile device, a multimedia device, a network server, a mainframe, one or more controllers, one or more microcontrollers, or any other general-purpose or application-specific computing device. The computer system 1200 may operate autonomously or semi-autonomously, or may read executable software instructions from the memory or storage device 1216 or a computer-readable medium (e.g., a hard drive, a CD-ROM, flash memory), or may receive instructions via the input device 1222 from a user, or any other source logically connected to a computer or device, such as another networked computer or server. Thus, in some embodiments, the computer system 1200 can also include any suitable device for reading computer-readable storage media.

Data, such as data acquired with an imaging system (e.g., a CT imaging system, a magnetic resonance imaging (MM) system, etc.) may be provided to the computer system 1200 from a data storage device 1216, and these data are received in a processing unit 1202. In some embodiment, the processing unit 1202 includes one or more processors. For example, the processing unit 1202 may include one or more of a digital signal processor (DSP) 1204, a microprocessor unit (MPU) 1206, and a graphics processing unit (GPU) 1208. The processing unit 1202 also includes a data acquisition unit 1210 that is configured to electronically receive data to be processed. The DSP 1204, MPU 1206, GPU 1208, and data acquisition unit 1210 are all coupled to a communication bus 1212. The communication bus 1212 may be, for example, a group of wires, or a hardware used for switching data between the peripherals or between any component in the processing unit 902.

The processing unit 1202 may also include a communication port 1214 in electronic communication with other devices, which may include a storage device 1216, a display 1218, and one or more input devices 1220. Examples of an input device 1220 include, but are not limited to, a keyboard, a mouse, and a touch screen through which a user can provide an input. The storage device 1216 may be configured to store data, which may include data such as atlas 118 (shown in FIG. 1), predictions 112 (shown in FIG. 1), attention maps 114 (shown in FIG. 1 and prediction bases 122 (shown in FIG. 1), whether these data are provided to, or processed by, the processing unit 1202. The display 1218 may be used to display images and other information, such as magnetic resonance images, patient health data, and so on.

The processing unit 1202 can also be in electronic communication with a network 1222 to transmit and receive data and other information. The communication port 1214 can also be coupled to the processing unit 1202 through a switched central resource, for example the communication bus 1212. The processing unit can also include temporary storage 1224 and a display controller 1226. The temporary storage 1224 is configured to store temporary information. For example, the temporary storage 1224 can be a random access memory.

Computer-executable instructions for analyzing medical images to detect and classify a medical condition according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly states, are possible and within the scope of the invention. The order and sequence of any process or method steps may be varied or re-sequenced according to alternative embodiments.

The invention claimed is:

1. A system for analyzing medical images to detect and classify a medical condition, the system comprising:
   an input for receiving a medical image;
   a convolutional neural network coupled to the input and configured to analyze the medical image to generate a prediction including a probability of the presence of the medical condition in the medical image;
   an atlas creation module coupled to the convolutional neural network and configured to generate an atlas comprising a set of image features and a set of training images, wherein each image feature is assigned with at least one training image associated with the medical condition;
   a prediction basis selection module coupled to the convolutional neural network and the atlas, the prediction basis selection module configured to create a prediction basis configured to provide an explanation for the prediction generated by the convolutional neural network, the prediction basis created by selecting at least one image feature and at least one training image assigned to the selected image feature from the atlas; and
   a display coupled to the convolutional neural network and the prediction basis selection module, the display configured to display at least the prediction and the prediction basis.

2. The system according to claim 1, wherein the medical condition has a plurality of subtypes.

3. The system according to claim 2, wherein the convolutional neural network is configured to generate a prediction indicating a probability of the presence of each of the plurality of subtypes of the medical condition and each image feature in the atlas is assigned with at least one training image associated with at least one of the plurality of subtypes of the medical condition.

4. The system according to claim 2, wherein the medical condition is intracranial hemorrhage (ICH) and the plurality of subtypes includes intraparenchymal hemorrhage (IPH), intraventricular hemorrhage (IVH), subdural hemorrhage (SDH), epidural hemorrhage (EDH) and subarachnoid hemorrhage (SAH).

5. The system according to claim 1, wherein the convolutional neural network is a deep convolutional neural network.

6. The system according to claim 1, wherein the convolutional neural network comprises a plurality of deep convolutional neural networks.

7. The system according to claim 1, wherein the medical condition is intracranial hemorrhage (ICH).

8. The system according to claim 1, further comprising a preprocessing module coupled to the input and the convolutional neural network, the preprocessing module configured to perform a multi-window conversion on the medical image received at the input.

9. The system according to claim 1, further comprising a preprocessing module coupled to the input and the convolutional neural network, the preprocessing module configured to perform slice interpolation.

10. The method according to claim 1, wherein the convolutional neural network comprises a plurality of deep convolutional neural networks.

11. The method according to claim 1, wherein the medical condition is intracranial hemorrhage (ICH).

12. A method for analyzing medical images to detect and classify a medical condition, the method comprising:
    receiving a medical image;
    analyzing the medical image using a convolutional neural network to generate a prediction including a probability of the presence of the medical condition in the medical image;
    creating a prediction basis configured to provide an explanation for the prediction generated by the convolutional neural network by selecting at least one image feature from an atlas comprising a set of image features and a set of training images, wherein each image feature is assigned with at least one training image associated with the medical condition; and
    displaying at least the prediction and the prediction basis on a display.

13. The method according to claim 12, wherein the medical condition has a plurality of subtypes.

14. The method according to claim 13, wherein the convolutional neural network is configured to generate a prediction indicating a probability of the presence of each of the plurality of subtypes of the medical condition and each image feature in the atlas is assigned with at least one training image associated with at least one of the plurality of subtypes of the medical condition.

15. The method according to claim 13, wherein the medical condition is intracranial hemorrhage (ICH) and the plurality of subtypes includes intraparenchymal hemorrhage (IPH), intraventricular hemorrhage (IVH), subdural hemorrhage (SDH), epidural hemorrhage (EDH) and subarachnoid hemorrhage (SAH).

16. The method according to claim 12, wherein the convolutional neural network is a deep convolutional neural network.

17. The method according to claim 12, further comprising a performing a multi-window conversion on the medical image received at the input.

18. The system according to claim 12, further comprising performing slice interpolation.

\* \* \* \* \*

UNITED STATES PATENT AND TRADEMARK OFFICE
CERTIFICATE OF CORRECTION

| | | |
|---|---|---|
| PATENT NO. | : 11,972,567 B2 | Page 1 of 1 |
| APPLICATION NO. | : 17/055068 | |
| DATED | : April 30, 2024 | |
| INVENTOR(S) | : Hyunkwang Lee et al. | |

It is certified that error appears in the above-identified patent and that said Letters Patent is hereby corrected as shown below:

In the Specification

Column 10, Line 37, "(MM)" should be --(MRI)--.

Signed and Sealed this
Second Day of July, 2024

Katherine Kelly Vidal
*Director of the United States Patent and Trademark Office*